United States Patent
Noack et al.

(10) Patent No.: US 10,422,023 B2
(45) Date of Patent: Sep. 24, 2019

(54) RECOVERY OF RARE EARTH ELEMENTS BY LIQUID-LIQUID EXTRACTION FROM FRESH WATER TO HYPERSALINE SOLUTIONS

(71) Applicant: CARNEGIE MELLON UNIVERSITY, a Pennsylvania Non-Profit Corporation, Pittsburgh, PA (US)

(72) Inventors: Clinton W. Noack, Pittsburgh, PA (US); Athanasios K. Karamalidis, Pittsburgh, PA (US); David A. Dzombak, Pittsburgh, PA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 526 days.

(21) Appl. No.: 15/138,117

(22) Filed: Apr. 25, 2016

(65) Prior Publication Data

US 2016/0312337 A1    Oct. 27, 2016

Related U.S. Application Data

(60) Provisional application No. 62/178,947, filed on Apr. 23, 2015.

(51) Int. Cl.
*B01D 11/04*    (2006.01)
*C22B 59/00*    (2006.01)
(Continued)

(52) U.S. Cl.
CPC .............. *C22B 59/00* (2013.01); *B01D 11/04* (2013.01); *B01D 11/0488* (2013.01);
(Continued)

(58) Field of Classification Search
CPC ...... Y02P 10/234; C22B 3/0008; C22B 59/00; C22B 60/026; B01D 11/02; B01D 11/023;
(Continued)

(56) References Cited

U.S. PATENT DOCUMENTS 3,122,414 A * 2/1964 Horner ................. C01F 11/005
                                                           423/10
3,302,993 A * 2/1967 Bray ....................... C01D 17/00
                                                           423/21.1

(Continued)

OTHER PUBLICATIONS

Giuseppe Modolo et al, "Thermodynamic study on the Synergistic Mixture of Bis(chlorophenyl)dithiophosphinic Acid and Tris(2-ethylhexyl)phosphate for Separation of Actinides(IIi) from Lanthanides(III)", Solvent Extraction and Ion Exchange, vol. 23: pp. 359-373. (Year: 2005).*

(Continued)

*Primary Examiner* — Joseph W Drodge
(74) *Attorney, Agent, or Firm* — Michael G. Monyok; David G. Oberdick

(57) ABSTRACT

The disclosure describes a method of extraction for optimal recovery of rare earth elements (REE). This includes the optimization of a liquid-liquid extraction technique for economic extraction of REE from chemically complex brines. Through the use of a model, operating conditions are altered to increase separation efficiency. The technique achieves >98% recovery of all rare earth elements in one fraction, while using small volumes of sample and reagents. The method of the present invention recovers REE from previously unexploited waste streams, without need for development of new process equipment and while keeping a small footprint because of the volumes involved.

17 Claims, 10 Drawing Sheets

(51) Int. Cl.
*C22B 3/00* (2006.01)
*G01N 1/40* (2006.01)
*C22B 3/26* (2006.01)

(52) U.S. Cl.
CPC ........ *B01D 11/0492* (2013.01); *C22B 3/0008* (2013.01); *G01N 1/4055* (2013.01); *G01N 2001/4061* (2013.01); *Y02P 10/234* (2015.11)

(58) Field of Classification Search
CPC . B01D 11/0284; B01D 11/0288; B01D 11/04; B01D 11/0484; B01D 11/0488; B01D 11/0492; G01N 1/40; G01N 1/4055; G01N 2001/4061
USPC ............. 210/634, 639; 423/2, 3, 8, 10, 21.5; 436/73, 81, 82, 178
See application file for complete search history.

(56) References Cited

U.S. PATENT DOCUMENTS

| | | | | |
|---|---|---|---|---|
| 3,582,290 | A * | 6/1971 | Grinstead et al. | C01D 3/18 423/157 |
| 3,615,170 | A * | 10/1971 | Hazen | C01G 56/001 423/21.5 |
| 3,702,233 | A * | 11/1972 | Gump et al. | C22B 59/00 423/21.1 |
| 4,394,269 | A * | 7/1983 | Tallent | G21F 9/12 210/690 |
| 4,871,464 | A * | 10/1989 | Kaneko | C01F 17/0006 210/682 |
| 5,258,167 | A * | 11/1993 | Takahashi | C01F 17/0006 210/634 |
| 5,750,081 | A * | 5/1998 | Smart | C22B 3/04 134/2 |
| 5,948,263 | A * | 9/1999 | Chaiko | C02F 1/26 210/634 |
| 6,312,654 | B1 * | 11/2001 | Modolo | C07F 9/16 252/184 |
| 2010/0116749 | A1 * | 5/2010 | Peterman | C07C 43/23 210/688 |
| 2010/0150798 | A1 * | 6/2010 | Peterman | C01F 17/0006 423/10 |
| 2013/0259776 | A1 * | 10/2013 | Heres | C22B 3/0012 423/9 |
| 2013/0313218 | A1 * | 11/2013 | Cox | B65D 41/0485 215/246 |

OTHER PUBLICATIONS

Daniel Magnusson, "Recovery Process of Actinides from Genuine Spent Nuclear Fuel using TODGA and BTBP Extractants", Thesis published by European Commision Joint Research Centre. (Year: 2008).*
Takaumi Kimura, Thermodynamic and Spectroscopic Studies on Am(III) and Eu(III) in the Extraction System of N,N,N',N'-Tetraoctyl-3-Oxapentane-1,5-Diamide in n-Dodecane/Nitric Acid, Nuclear Science and Engineering Directorate, Japan Atomic Energy Agency, Tokai-mura, Ibaraki, Japan. (Year: 2011).*
DeSouky, "Liquid-Liquid Extraction of Rare Earth Elements from Sulfuric Acid Solutions", published by University of Leeds. (Year: 2006).*
Agatemor, C. et al. "Matrix effects in inductively coupled plasma mass spectrometry: a review." Analytica chimica acta 706, No. 1 (2011): 66-83.
Jaffe, R. et al. "Securing Materials for Emerging Technologies." American Physical Society (APS) panel on Public Affairs and Materials Research Society (NRS) (2011).
Aries, S. et al. "A Routine Method for Oxide and Hydroxide Interference Corrections in ICP-MS Chemical Analysis of Environmental and Geological Samples." Geostandards and Geoanalytical Research 24, No. 1 (2000): 19-31.
Barbot, E. et al. "Spatial and temporal correlation of water quality parameters of produced waters from Devonian-age shale following hydraulic fracturing." Environmental science & technology 47, No. 6 (2013): 2562-2569.
Bau, M. et al. "Anthropogenic origin of positive gadolinium anomalies in river waters." Earth and Planetary Science Letters 143, No. 1-4 (1996): 245-255.
Benkhedda, K. et al. "Determination of sub-parts-per-trillion levels of rare earth elements in natural waters by inductively coupled plasma time-of-flight mass spectrometry after flow injection on-line sorption preconcentration in a knotted reactor" Presented at the 2001 European Winter Conference on Plasma Spectrochemistry, Lillehammer, Norway, Feb. 4-8, 2001. Journal of Analytical Atomic Spectrometry 16, No. 9 (2001): 995-1001.
Doehlert, David H. "Uniform shell designs." Applied statistics (1970): 231-239.
Elimelech, M. et al. "The future of seawater desalination: energy, technology, and the environment." science 333, No. 6043 (2011): 712-717.
Erel, Y. et al. "Modeling of rare-earth element partitioning between particles and solution in aquatic environments." Geochimica et Cosmochimica Acta 57, No. 3 (1993): 513-518.
Ferreira, S. et al. "Doehlert matrix: a chemometric tool for analytical chemistry." Talanta 63, No. 4 (2004): 1061-1067.
Fu, Q. et al. "On-line preconcentration with a novel alkyl phosphinic acid extraction resin coupled with inductively coupled plasma mass spectrometry for determination of trace rare earth elements in seawater." Talanta 72, No. 4 (2007): 1248-1254.
Haley, B. et al. "Complete separation of rare earth elements from small volume seawater samples by automated ion chromatography: method development and application to benthic flux." Marine Chemistry 82, No. 3 (2003): 197-220.
Halicz, L. et al. "On-line method for inductively coupled plasma mass spectrometric determination of rare earth elements in highly saline brines." Journal of Analytical Atomic Spectrometry 11, No. 9 (1996): 811-814.
Haluszczak, L. et al. "Geochemical evaluation of flowback brine from Marcellus gas wells in Pennsylvania, USA." Applied Geochemistry 28 (2013): 55-61.
Hirata, S. et al. "Determination of rare earth elements in seawater by on-line column preconcentration inductively coupled plasma mass spectrometry." Talanta 58, No. 6 (2002): 1185-1194.
Jenner, G. A. et al. "ICP-MS—a powerful tool for high-precision trace-element analysis in earth sciences: evidence from analysis of selected USGS reference samples." Chemical Geology 83, No. 1-2 (1990): 133-148.
Kajiya, T. et al. "Determination of rare earth elements in seawater by inductively coupled plasma mass spectrometry with on-line column pre-concentration using 8-quinolinole-immobilized fluorinated metal alkoxide glass." Spectrochimica Acta Part B: Atomic Spectroscopy 59, No. 4 (2004): 543-550.
Katarina, R. et al. "High-capacity chitosan-based chelating resin for on-line collection of transition and rare-earth metals prior to inductively coupled plasma-atomic emission spectrometry measurement." Talanta 79, No. 5 (2009): 1252-1259.
Kim, I. et al. "Analytical artifacts associated with the chelating resin extraction of dissolved rare earth elements in natural water samples." Aquatic geochemistry 16, No. 4 (2010): 611-620.
Kühn, M. et al. "Improved detection of transition and rare earth elements in marine samples with the CETAC DSX-100 preconcentration/matrix elimination system and ICP-MS." Fresenius' journal of analytical chemistry 367, No. 5 (2000): 440-444.
Kulaksiz, S. et al. "Anthropogenic dissolved and colloid/nanoparticle-bound samarium, lanthanum and gadolinium in the Rhine River and the impending destruction of the natural rare earth element distribution in rivers." Earth and Planetary Science Letters 362 (2013): 43-50.
Kumar, S. et al. "Matrix separation and preconcentration of rare earth elements from seawater by poly hydroxamic acid cartridge followed by determination using ICP-MS." Desalination 281 (2011): 49-54.

(56) References Cited

OTHER PUBLICATIONS

Lawrence, M. et al. "Rare Earth Element Concentrations in the Natural Water Reference Materials (NRCC) NASS-5, SASS-4 and SLEW-3." Geostandards and Geoanalytical Research 31, No. 2 (2007): 95-103.
Lee, P. et al. "Dissolution of D 2 EHPA in liquid—liquid extraction process: Implication on metal removal and organic content of the treated water." Water research 45, No. 18 (2011): 5953-5958.
Lund, J.W. et al. "Direct utilization of geothermal energy 2010 worldwide review." Geothermics 40, No. 3 (2011): 159-180.
McGill, R. et al. "Variations of box plots." The American Statistician 32, No. 1 (1978): 12-16.
McGinnis, C. et al. "Characterisation of Memory Effects and Development of an Effective Wash Protocol for the Measurement of Petrogenetically Critical Trace Elements in Geological Samples by ICP-MS." Geostandards and Geoanalytical Research 21, No. 2 (1997): 289-305.
Murali M. et al. "Microbial community changes in hydraulic fracturing fluids and produced water from shale gas extraction." Environmental science & technology 47, No. 22 (2013): 13141-13150.
Möller, P. et al. "Determination of rare earth elements in seawater by inductively coupled plasma-mass spectrometry" Spectrochimica Acta Part B: Atomic Spectroscopy 47, No. 12 (1992): 1379-1387.
Nash, K. "A review of the basic chemistry and recent developments in trivalent f-elements separations." Solvent Extraction and Ion Exchange 11, No. 4 (1993): 729-768.
Nelson, A. et al. "Matrix complications in the determination of radium levels in hydraulic fracturing flowback water from Marcellus Shale." Environmental Science & Technology Letters 1, No. 3 (2014): 204-208.
Noack, C. et al. "Rare earth element distributions and trends in natural waters with a focus on groundwater." Environmental science & technology 48, No. 8 (2014): 4317-4326.
Oliveira, E. P. et al. "Determination of trace metals in high-salinity petroleum produced formation water by inductively coupled plasma mass spectrometry following on-line analyte separation/preconcentration." Journal of Analytical Atomic Spectrometry 26, No. 3 (2011): 578-585.
Raso, M. et al. "Simultaneous determinations of zirconium, hafnium, yttrium and lanthanides in seawater according to a co-precipitation technique onto iron-hydroxide." Talanta 116 (2013): 1085-1090.
Shabani, M. B. et al. "Determination of trace lanthanides and yttrium in seawater by inductively coupled plasma mass spectrometry after preconcentration with solvent extraction and back-extraction." Analytical Chemistry 62, No. 24 (1990): 2709-2714.
Shannon, M. A. et al. "Science and technology for water purification in the coming decades." Nature 452, No. 7185 (2008): 301-310.
Shaw, T.J. et al. "A preconcentration/matrix reduction method for the analysis of rare earth elements in seawater and groundwaters by isotope dilution ICPMS." Analytical chemistry 75, No. 14 (2003): 3396-3403.
Stetzenbach, K. J. et al. "Testing the Limits of ICP-MS: Determination of Trace Elements in Ground Water at the Part-Per-Trillion Level." Groundwater 32, No. 6 (1994): 976-985.
Thompson, M. et al. "Harmonized guidelines for the use of recovery information in analytical measurement." Pure and applied chemistry 71, No. 2 (1999): 337-348.
United States Department of Energy. "Critical materials strategy." US Department of Energy, 2010.
"Annual Energy Outlook 2014 with projections to 2040." US Energy Information Administration (Apr. 2014).
Vicente, O. et al. "Determination of some rare earth elements in seawater by inductively coupled plasma mass spectrometry using flow injection preconcentration." Spectrochimica Acta Part B: Atomic Spectroscopy 53, No. 9 (1998): 1281-1287.
Vidic, R. D. et al. "Impact of shale gas development on regional water quality." Science 340, No. 6134 (2013): 1235009.
Weaver, B. et al. "TALSPEAK: A new method of separating americium and curium from the lanthanides by extraction from an aqueous solution of an aminopolyacetic acid complex with a monoacidic organophosphate or phosphonate." No. ORNL-3559. Oak Ridge National Lab., Tenn., 1964.
Wen, B. et al. "Preconcentration of ultratrace rare earth elements in seawater with 8-hydroxyquinoline immobilized polyacrylonitrile hollow fiber membrane for determination by inductively coupled plasma mass spectrometry." Analyst 124, No. 4 (1999): 621-626.
Willie, S. N. et al. "Determination of transition and rare earth elements in seawater by flow injection inductively coupled plasma time-of-flight mass spectrometry." Spectrochimica Acta Part B: Atomic Spectroscopy 56, No. 9 (2001): 1707-1716.
Zawisza, B. et al. "Determination of rare earth elements by spectroscopic techniques: a review." Journal of Analytical Atomic Spectrometry 26, No. 12 (2011): 2373-2390.
Zhang, T. et al. "Preconcentration of rare earth elements in seawater with poly (acrylaminophosphonic dithiocarbamate) chelating fiber prior to determination by inductively coupled plasma mass spectrometry." Analytical Chemistry 70, No. 18 (1998): 3964-3968.
Zhu, Y. et al. "Determination of REEs in seawater by ICP-MS after on-line preconcentration using a syringe-driven chelating column." Talanta 78, No. 3 (2009): 891-895.
Gregory, K. B. et al. "Water management challenges associated with the production of shale gas by hydraulic fracturing." Elements 7, No. 3 (2011): 181-186.

* cited by examiner

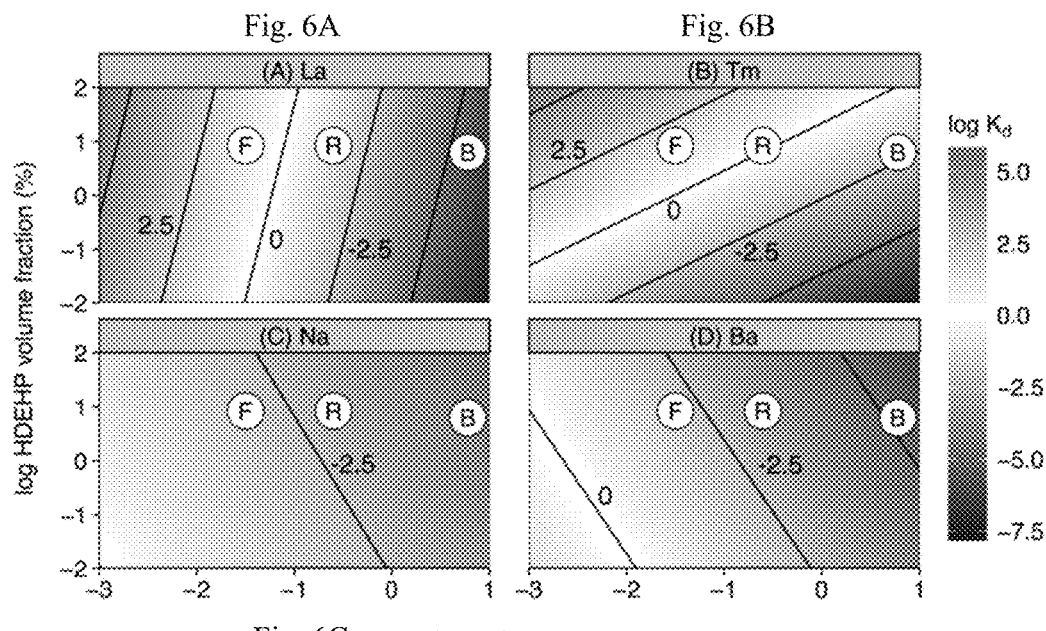
Fig. 6A  Fig. 6B
Fig. 6C  Fig. 6D
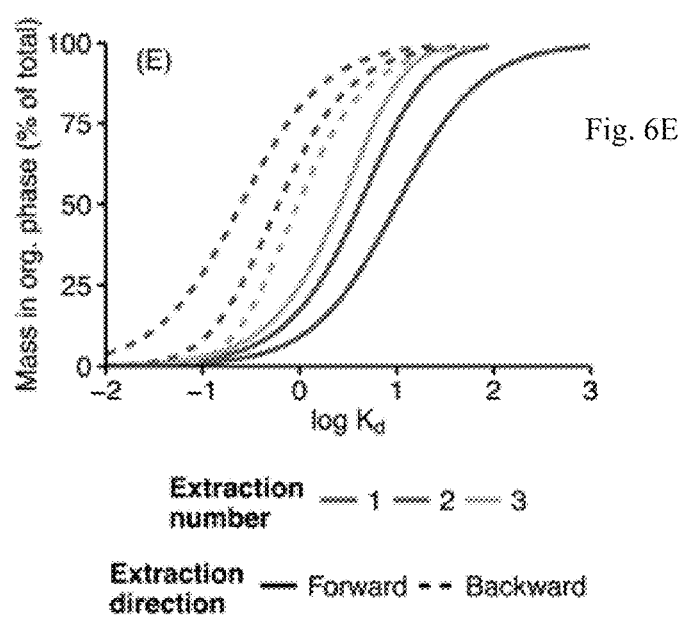
Fig. 6E

Fig. 7A
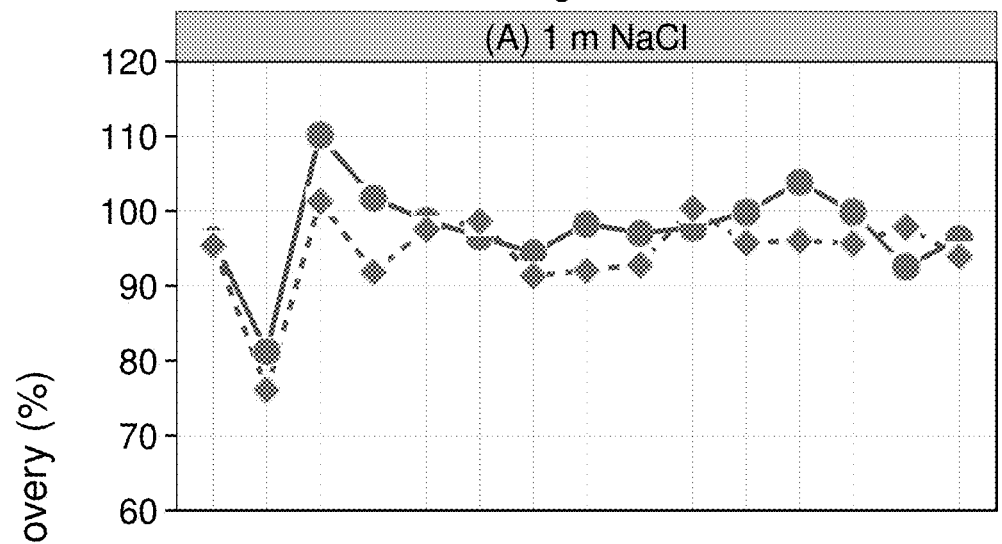
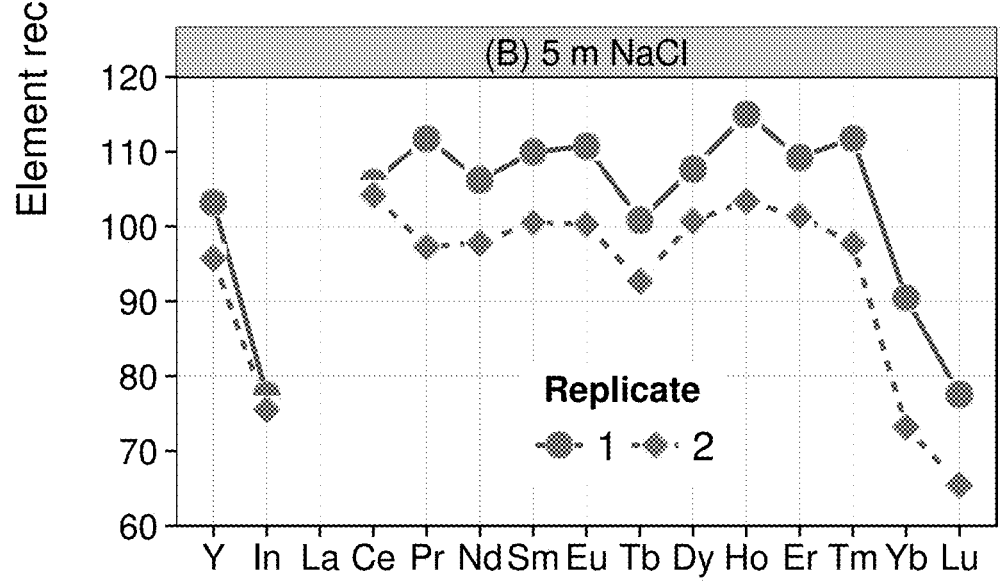
Fig. 7B

RECOVERY OF RARE EARTH ELEMENTS BY LIQUID-LIQUID EXTRACTION FROM FRESH WATER TO HYPERSALINE SOLUTIONS

CROSS-REFERENCE TO RELATED APPLICATIONS

This application claims the benefit under 35 U.S.C. § 119 of Provisional Ser. No. 62/178,947, filed Apr. 23, 2015, which is incorporated herein by reference.

STATEMENT REGARDING FEDERALLY SPONSORED RESEARCH

This invention was made with Government support under DE-FE0004000 awarded by the U.S. Department of Energy. The Government has certain rights in this invention.

BACKGROUND OF THE INVENTION

This invention relates generally to the recovery of rare earth metals. More specifically, the invention relates to the recovery of rare earth elements from fresh water to hypersaline solutions using liquid-liquid extraction methods.

The rare earth elements (REE) are among the most frequently cited critical materials for clean energy and high-tech manufacturing. The unique and varied properties of REE have led to their application in more consumer products than nearly any other element group. REE are mostly obtained from mining and processing of REE-enriched ores. However, mining is expensive and laborious with a significant environmental burden.

Aqueous byproduct or waste streams, both natural and industrial, are potential sources of the REE and other critical materials. With increasing global interest in geothermal energy, development of unconventional oil and gas resources (e.g. hydraulic fracturing of organic rich shales), and desalination technologies, large volumes of waste brines are being managed and processed at great expense. Development of technologies for recovery of valuable byproducts, such as the REE, from these waste streams could improve the economies of these technologies. Development of such technologies requires accurate determination of the source REE concentration in order to develop and implement recovery systems. However, precise quantitation of REE in complex matrices like brines is a significant challenge for conventional instrumentation such as inductively coupled plasma mass spectrometry (ICP-MS).

There exists a dearth of methodologies in the analytical literature for quantitation of REE in brines by ICP-MS. Many approaches have been applied for separation and concentration of REE from aqueous media including solid-phase extraction (SPE), co-precipitation (co-ppt), and liquid-liquid extraction (LLE). However, nearly all studies in the analytical literature have focused on fresh water or seawater matrices, neglecting hypersaline waters (i.e. more concentrated than seawater, ~0.7 M NaCl). Despite this deficiency, approximately 14% of published measurements of REE in groundwater constitute brine samples (greater than 1 eq/kg ionic strength), with these analyses utilizing methodologies not explicitly validated for extreme salinity.

Commonly applied separation techniques such as SPE and co-ppt may lack the robustness necessary to analyze REE in hypersaline brines. For example, high dissolved organic carbon may lead to fouling of column-based SPE while high dissolved metal loads may lead to saturation of the surface sites responsible for REE binding. Oliveira, et al. ascribed diminished Zn recovery in 166% salinity produced water to competitive sorption of matrix cations on their iminodiacetate resin. Similarly, excessive cations in hypersaline solutions may screen the REE from sorption sites during co-ppt, a phenomenon noted by Nelson, et al. for Ra determination in produced waters from the Marcellus Shale by both $BaSO_4$ and $MnO_2$ co-ppt. Moreover, at the elevated pH necessary for SPE and co-ppt techniques, the formation of energetically favorable, neutral- or negatively-charged aqueous complexes of the REE (with both organic and inorganic ligands) can further limit REE-particle partitioning.

Liquid-liquid extractions are potentially robust to all of these conditions and represent an attractive alternative for REE separation from hypersaline solutions. Liquid-liquid extraction of REE from highly acidic solutions has been thoroughly studied for separation of lanthanides and actinides during nuclear fuel reprocessing; elevated pH is not required of LLE techniques. Moreover, electrolyte theory dictates that increased sample salinity should enhance chemical partitioning (through salting out of neutral/micellar REE-organic ligand complexes from the aqueous feed to the organic solvent) and physical phase separation (by collapsing the electric double layer of the organic droplets, hastening coalescence). A primary obstacle in extraction of hydrophilic metals to a hydrophobic, organic phase is the dehydration of the metal cations in the aqueous phase. However, increasing salt concentrations decrease the effective concentration of water in the solution available for hydration of the metal cations, improving the energetics of the extraction.

BRIEF SUMMARY OF THE INVENTION

According to one embodiment of the present invention is process that includes the optimization of an analytical technique for economic extraction of rare earth elements (REE) from chemically complex brines. The recovered REE can be subjected to analysis or further testing, such as ICP-MS. Through the use of a mathematical model, operating conditions are altered to increase separation efficiency. The technique provides increased (20-40% greater overall recovery) and more consistent recovery of the REE than previously published techniques, while using small volumes of sample and reagents. The method of the present invention extracts and economically recovers REE from previously unexploited waste streams, without need for development of new process equipment and while keeping a small footprint because of the volumes involved.

More specifically, the invention is a liquid-liquid extraction (LLE) method, typically used for aqueous solutions with ionic strength of <0.7M NaCl, that has been modified and optimized for greater salt concentrations. In one embodiment, the process has been modified by using one chelating agent instead of two, minimizing the cost of extraction, and extended the technology to work with aqueous solutions of ionic strength up to 5M NaCl. The method incorporates an optimization scheme for adjusting the solution parameters in order to achieve >98% recovery of all rare earth elements (i.e. lanthanides) in one fraction. The invention also addresses the existing gap in analytical methodologies for reliable measurement of REEs in hypersaline solutions and lowers the actual sample volume necessary for an REE analysis from 1 L to 10 mL.

The present invention successfully separates all lanthanides, except for the end members of the lanthanide series at very high ionic strength, Yb and Lu (recovered at ~75% in 5 M NaCl), from hypersaline aqueous solutions. The separation results in a new fraction with concentrated mixture of lanthanides in pure form. Further separation of individual lanthanides is necessary. The invention is accompanied by an optimization scheme which considers the composition of the aqueous medium and informs the analyst about the necessary adjustments to be made to the liquid-liquid extraction parameters in order for high recovery (>98%) of lanthanides to be achieved.

Advantages of the present invention include: extraction of REE are possible with a minimum consumption of energy; selectivity; utility when other standard separation methods fail (e.g. due to clogging, fouling, etc.), require expensive equipment, or have high energy cost; separation can be done at high pressure and/or temperature, if necessary (for example, avoiding precipitation of silica in treatment of high temperature geothermal fluids); it is a well-known and established extraction technology to the industry (liquid-liquid extraction is commonly employed in industrial applications such as hydrometallurgy, fine chemical industry, petroleum industry, bulk chemical industry, biotechnology); it can be designed as a series of counter-current separators to enhance the efficiency of the extraction system; utilizes chemistry and processes which are well understood, but applies them to a previously unexploited source after optimization of operating conditions for the new target matrix; requires small volumes of reagents and source stream, which will limit the footprint of full-scale deployment; and high (>92%) recovery has been demonstrated for a range of simulated brine chemistries that include variable electrolyte concentrations as well as competing ions.

BRIEF DESCRIPTION OF THE SEVERAL VIEWS OF THE DRAWINGS

In FIGS. 2B and 2D, $^{135}Ba^{16}O^+$ rate is inferred from 23 replicate analyses of a 200 ppb Ba standard after blank subtraction.

FIGS. 6A-6E illustrates the summary of model-based optimization of LLE operating condition.

FIG. 7A-7B presents the REE recovery by LLE method in simple, saline solutions. Initial REE concentrations were 500 ppt (each element) in all experiments.

DETAILED DESCRIPTION OF THE INVENTION

Complex, hypersaline brines—including those co-produced with oil and gas, rejected from desalination technologies, or used as working fluids for geothermal electricity generation—could contain critical materials such as the rare earth elements (REE) in recoverable concentrations. Analysis of these critical materials in complex, aqueous matrices is necessary for evaluation and implementation of systems aimed at recovering those materials. However, most analytical methods for measuring trace metals have not been validated for highly saline and/or chemically complex brines.

According to one embodiment, the method of the present invention modifies and optimizes a liquid-liquid extraction (LLE) technique, using bis(2-ethylhexyl) phosphate as the extractant in a heptane diluent. Moreover, with proper characterization of the natural samples of interest, the method can be deployed for accurate analysis of REE in hyper-saline and chemically complex brines.

Figure 1:
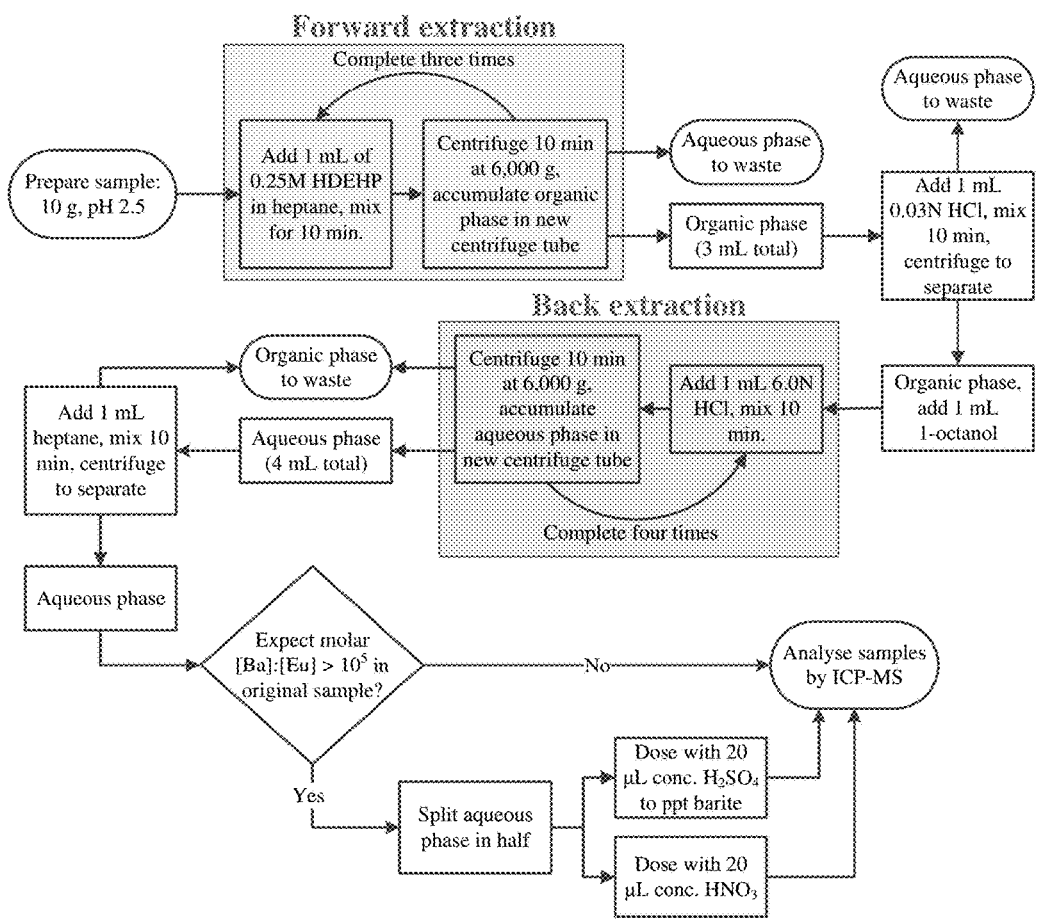
FIG. 1 is a flowsheet of the liquid-liquid extraction method according to one embodiment for separation and concentration of REE from small volume, hypersaline brines.

In one example embodiment, a common ligand used for REE complexation and extraction, bis(2-ethylhexyl) phosphate (HDEHP), is used in a heptane diluent. A schematic flowsheet of the process is shown in FIG. 1. As shown in FIG. 1, the process comprises sample preparation, followed by three cycles of extraction, whereby the REE is complexed by the HDEHP ligand and brought into the organic phase, leaving an REE-free, waste brine. Matrix elements are rinsed from the organic phase with dilute acid, and, finally, the REE is recovered by four cycles of elution with strong acid. This REE-loaded aqueous phase is then analyzed by ICP-MS.

In this example, synthetic brine solutions were adjusted to pH 2.5 in 50 mL, PP centrifuge tubes with $HNO_3$ and subsequently split into 10 g aliquots in 15 mL PP centrifuge tubes for replicate experiments. Next, 1 mL of 0.25 M HDEHP in heptane was added to the aqueous solution. HDEHP was used as complexing agent for REE. The phases were emulsified and mixed end over end for 10 minutes. The phases were separated by centrifugation at 6,000 g for 10 minutes and the light organic phase was removed from the centrifuge tube via pipette and accumulated in a new centrifuge tube, retaining the aqueous phase in the original tube. This process, whereby the REE are complexed with HDEHP and partitioned into the heptane (termed forward extraction), was completed a total of three times. Following the third forward extraction, the aqueous phase was discarded.

To remove any matrix (Na, Fe, etc.) and interfering species (i.e. Ba) that partitioned during forward extraction, the accumulated organic phase (3 mL total) was rinsed with 1 mL of pH 1.5 HCl. This mixture was emulsified and separated by the same methods as the forward extraction. Once separated, the dense aqueous phase was removed via pipette and discarded.

A concentrated acid solution was used to dissociate the REE-HDEHP complexes and return the REE to an aqueous phase (termed back extraction). To decrease the REE-HDEHP complexation strength and encourage complete recovery, 1 mL of 1-octanol was added to the organic phase. Back extraction was achieved with four, sequential steps of stripping with 1 mL of 6.0 N HCl (collecting the eluted REE in a total of 4 mL acid). As with the forward extraction, the sample was emulsified and mixed end over end for 10 minutes and then separated via centrifugation at 6,000 g. After centrifugation the aqueous phase was removed via pipette and accumulated in a separate centrifuge tube, retaining the organic phase in the original tube. Following the four back-extractions, the organic phase was discarded.

The collected acid volume (4 mL) was then rinsed with 1 mL of heptane to remove any dissolved organics from the aqueous phase. Phase mixing and separation were accomplished in the same manner as all other steps. Following centrifugation, the dense aqueous phase was removed and analyzed.

Preliminary experiments (see Supporting Information (SI), below, SI1, "Barium removal"; FIGS. 2A-2D) indicated that, while Ba was being successfully removed in the course of the LLE (>99.9% average reduction) and that the HEHe-mode collision cell in the ICP-MS was successfully limiting $^{135}Ba^{16}O^+$ interferences with $^{151}EU^+$ ($^{135}Ba^{16}O^+$: $^{135}Ba^+$ ~0.2% on average), initial Ba concentrations were so high that ppb level, background Eu concentrations were observed (SI2. "Background REE concentration", FIG. 3). Thus, in order to accurately determine Eu in these synthetic brines an additional step is used, where an aliquot of the final, collected acid volume was dosed with 20 μL concentrated sulfuric acid ($H_2SO_4$) to precipitate any remaining barium as barite ($BaSO_4$). Efficiency of Ba removal after $H_2SO_4$ addition is compared in FIGS. 2B and 2D. It should be noted that this step is unnecessary for samples without Ba.

The methodology of Jenner, et al. as modified by McGinnis, et al. was employed to correct for matrix effects, isobaric interferences, and instrument drift during ICP-MS analysis. Details of this methodology are provided in the SI3. "Internal-external standardization for analytical corrections." Typical analytical uncertainty was between 3 and 5%. Because of high backgrounds of Gd in the laboratory and high Ba in the experiments, oxide corrections for $^{137}Ba^{16}O^+$ interference on $^{151}EU^+$ and $^{157}Gd^{16}O^+$ were applied as in Aries, et al. after ICP-MS analysis.

Preparation of Synthetic Brines

In addition to optimization of operating parameters, the process must be validated for complex brine solutions. The complexity of the brine is a function of background salinity and interfering compounds (both inorganic and organic). This was investigated in two stages. First, simple solutions (1 m and 5 m NaCl) were used to evaluate feasibility. Second, compositional complexity was explored via a uniform shell experimental design, varying NaCl, Fe, and dissolved organic carbon (DOC; represented by pentanoic acid) concentrations. The concentrations of background salinity and interfering compounds were chosen to match reported value ranges found in studies of produced waters from unconventional gas development in the Marcellus Shale, however the range of compositions studied is similar to other deep, basinal brines. Concentrations of the matrix components ranged between (nominal value in parentheses): 0.5-3.5 mol/kg solution (2.0 m) for NaCl, 5.4-75 ppm (40 ppm) for Fe, and 37-363 ppm as C (200 ppm as C) for DOC. Details of each experiment are provided in SI6. "Preparation of synthetic brines" (Table S2). The concentration of each REE (and indium) was held constant at 500 ppt (parts per trillion) in all experiments. Results of these experiments were analyzed by multiple linear regression (MLR) to determine which parameters of the synthetic brine influenced the recovery most strongly.

Optimization of Liquid-Liquid Operation Parameters

Preliminary experiments utilizing LLE conditions described by Shabani, et al. and Lawrence and Kamber were unable to achieve high or consistent recovery of the REE, (see SI7. "Recovery of REE, using previously published LLE conditions", FIGS. 4A-4D). It should be noted that both Shabani, et al. and Lawrence and Kamber employed a mixture of mono- and di-ester phosphonic acids as the chelating ligand. This ligand combination was also explored, however preliminary experiments provided poor results compared to the pure diester (HDEHP) under the same conditions and was not studied further (FIG. 5).

In order to optimize method performance, a linear model (Equation 1) was fit by ordinary least-squares in R using the datasets of Kimura. The relationship between the response (organic-aqueous distribution coefficient, $K_d$) and each of the predictors (solution acidity [ACY], and ligand concentration [L]) is shown to be independently log linear. Therefore the variables in this model correspond to log values. Data for fitting of this model were extracted from FIG. 1 of Kimura for $K_d$ vs. [ACY] at constant [L] and from FIG. 1 of Kimura for $K_d$ vs. [L] at constant [ACY]. This estimation of parameter values reflects the dependence of log $K_d$ on log[ACY] ($\beta_{ACY}$) and on log[L] ($\beta_L$) as well as a constant intercept ($\beta_0$).

$$\log K_d = \beta_{ACY}*\log[ACY] + \beta_L*\log[L] + \beta_0 \quad (1)$$

The extraction of REE from the aqueous to the organic phase is calculated using the fitted $K_d$ values based on mass balance. The fraction of REE mass in the organic phase ($R_{org}$) for equilibrium between an aqueous phase (with volume $V_{aq}$) and an organic phase (with volume $V_{org}$) is calculated by Equation 2.

$$Rorg = \frac{1}{1 + \frac{Vaq}{Vorg}*Kd^{-1}} \quad (2)$$

The system can be represented as independent LLE in series since the phases are separated after each extraction step. Thus, the overall partitioning of REE from the brine to the organic phase ($R_{tot}$) in the forward extraction can be calculated for n sequential extractions with Equation 3. This allows for determination of the number of extractions necessary for quantitative recovery of REE. The analysis is simply reversed to examine the elution properties of REE from the organic phase back into an aqueous phase.

$$Rtot = \Sigma_{i=1}^{n} Rorg(1-Rorg)^{i-1} \quad (3)$$

This analysis is meant to provide a "best guess" as to the optimal method parameters without requiring additional experimentation. The inherent limitation of this approach is the uncertain extensibility of the original data to both a modified methodology (i.e. small volumes, changed organic diluent, mixed analyte solutions, low initial REE concentration) and unique matrices (i.e. acidified brines vs. HCl).

Therefore post hoc analysis of preliminary experiments for parameter optimization was done qualitatively. Moreover, since $K_d$ values were not calculated as part of this study, model validation with new experimental results was not performed.

Multiple, Linear-Regression of Organic-Aqueous Distribution Coefficients

Fractionation of the REE observed in preliminary experiments (FIGS. 4A-4D) can be qualitatively reconciled from multiple, linear-regression analysis. FIGS. 6A-6D shows that the rinse step (labeled "R") creates strong stripping conditions (log Ka<-1) for the LREE (La; FIG. 6A) while the back extraction (labeled "B") may provide inadequate acidity to recover the HREE (Tm; FIG. 6B) once partitioned. Thus the operating conditions must be altered to achieve consistent and quantitative recovery for all REE.

Referring to FIGS. 6A-6D, organic-aqueous distribution coefficient ($K_d$; Equation 1) contours as a function of acidity and HDEHP volume fraction for La, Tm, Na, and Ba calculated with data from Kimura and Kimura. LLE operating conditions for forward extractions (F), matrix rinse (R), and back extractions (B) suggested by Shabani, et al. are noted. (E) Equilibrium partitioning for triplicate forward and backward extractions as a function of organic/aqueous distribution coefficient ($K_d$). Partitioning calculated by Equation 2 with $V_{aq}/V_{org}=10$ for forward extraction and 0.25 for backward extraction.

The final values of initial acidity, HDEHP concentration, rinse acidity, and strip acidity were selected from this model to ensure (1) exclusion of Na and Ba during forward extraction, (2) rejection of Na and Ba during matrix rinsing, and (3) minimal loss of REE during all steps. Parameters were optimized by examining FIG. 6A-D over reasonable [ACY] and [L] ranges to achieve $K_d$ values required for quantitative recovery (FIG. 6E). The final eluent acidity was determined without considering the effects of octanol addition beyond dilution of [L].

Using FIG. 6E it can be shown that forward extractions require a log $K_d$>1.6 to achieve >99% partitioning to the organic phase after triplicate extractions. Further, the conditions of the rinse phase must maintain log $K_d$>1.4 in order to retain >99% REE in the organic phase from one rinse step. Finally, to achieve >99% recovery of REE during triplicate back extractions, conditions must create log $K_d$<-1.2.

The conditions ([ACY] and [L]) required to achieve these distribution coefficients can be found by examining FIGS. 6A-6D. By decreasing the initial acidity to <$10^{-2}$ N (i.e. pH>2) the initial extraction of REE can be enhanced without significantly increasing partitioning of Na or Ba. From this analysis, an initial sample pH of 2.5 was chosen. Dissolution of the organic phase, which has been shown to diminish partitioning, should be limited below pH 3. Similarly, by reducing the acidity of the rinse step to <$10^{-1.5}$ N (i.e. pH>1.5) salts such as Na and Ba (FIGS. 6C, 6D) can be eluted while retaining the REE (FIGS. 6A, 6B). While this simplified analysis suggests that triplicate back extraction steps should achieve quantitative recovery of all REE, preliminary experiments (FIGS. 4C, 4D) showed that the HREE were incompletely recovered. From these results an additional elution step was added to the procedure. As discussed previously, the chemistries of the LLE and the brine samples described here are different from that of the data used to fit the models of FIGS. 6A-6D. As a result experimental deviation from this equilibrium model was likely.

Interferences of Synthetic Brine Constituents

Results for REE recovery from simple solutions of 1 m and 5 m NaCl, the REE are presented in FIGS. 7A-7B. In the 1 m NaCl solution, REE recovery was consistently between 90 and 110%, however, indium recovery was markedly lower: 76 and 81% in duplicate experiments. Similar results were observed in the high salinity test (5 m NaCl), except that the heaviest two lanthanides, Yb and Lu, were recovered at a much lower rate, averaging 82% for Yb and 72% for Lu. Recovery of indium from the 5 m NaCl solution (mean, 76%) matched the recovery observed in the 1 m NaCl solution indicating that this diminished recovery is likely not a function of the salt concentration.

In the Kimura datasets, the HREE interact more strongly with HDEHP than do the LREE, making them more difficult to elute, even at high acidity. While not directly comparable (because the salinity and initial REE concentrations differ) a small increase in HREE recovery appears to result from the additional back-extraction step (FIG. 7B vs. FIGS. 4C, 4D), from ~60% for Yb, Lu with 3 steps to 70-80% with 4 steps. Similarly Tm recovery (80-90%, FIG. 4C,D) is increased substantially (100-110%, FIG. 7B). Given the limitations of the equilibrium-partitioning model developed to optimize extraction conditions, it is likely that the strength of partitioning (to the organic phase) for the HREE was underestimated. The observed 70% recovery in four steps for Lu implies an actual $K_d \approx -0.3$, compared to $K_d \approx -0.9$ required for >99% recovery in 4 steps.

Figure 8:
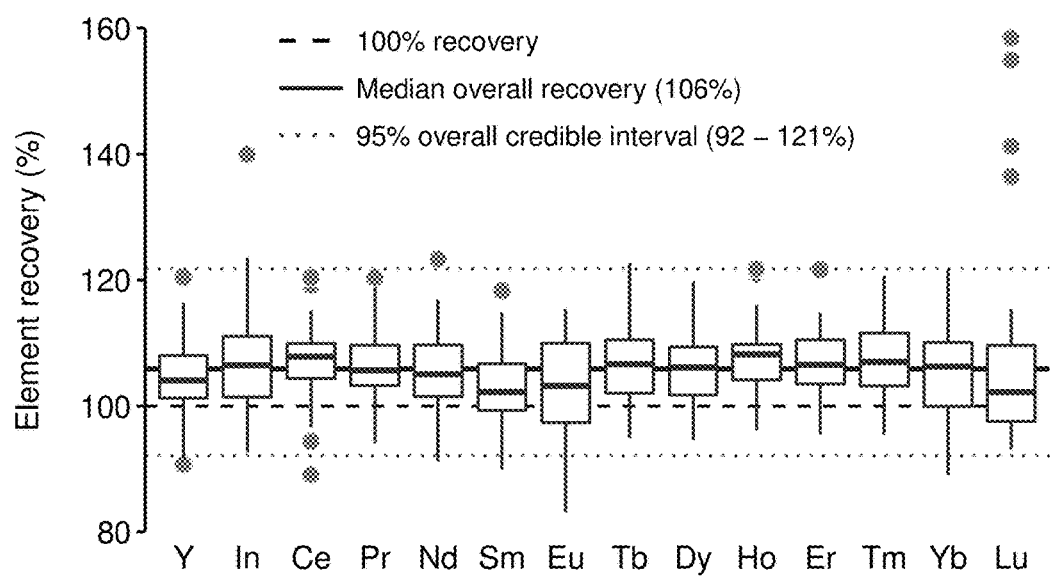
FIG. 8 shows distributions of elemental recovery in Doehlert matrix samples by LLE methodology.
Figure 9:
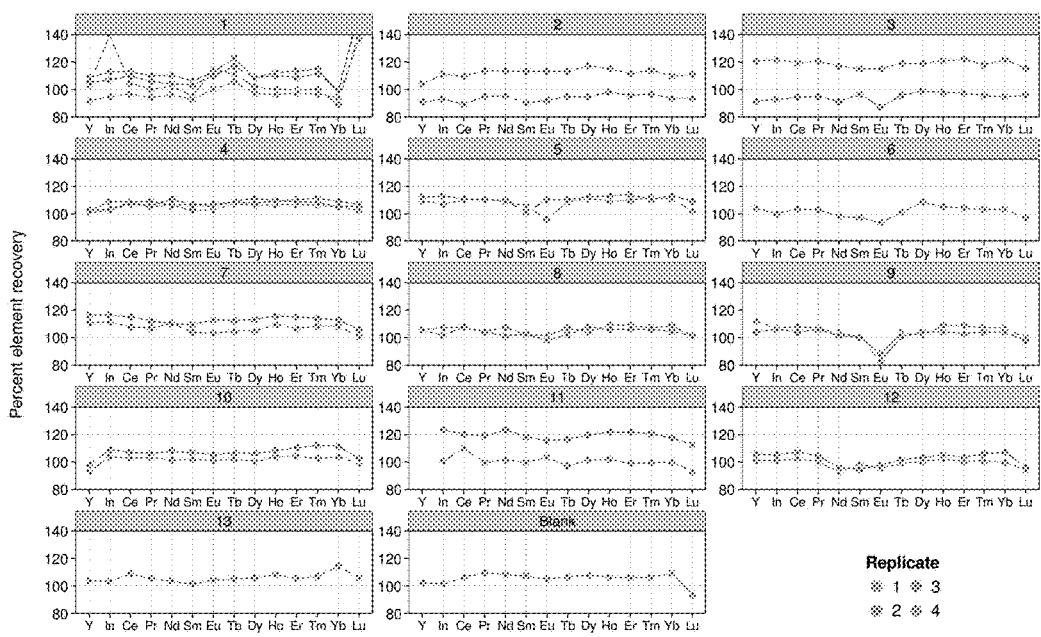
FIG. 9 displays elemental recovery in Doehlert matrix samples by LLE methodology.
Figure 10A:
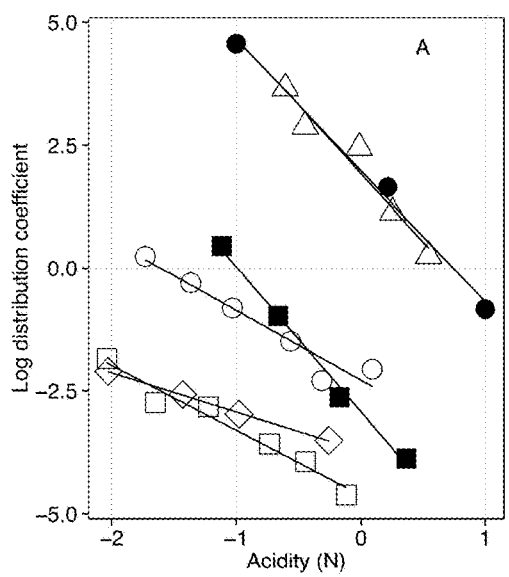
FIGS. 10A-10B presents organic-aqueous distribution coefficients of selected elements as functions of acidity (A) and HDEHP volume fraction (B).
Figure 10B:
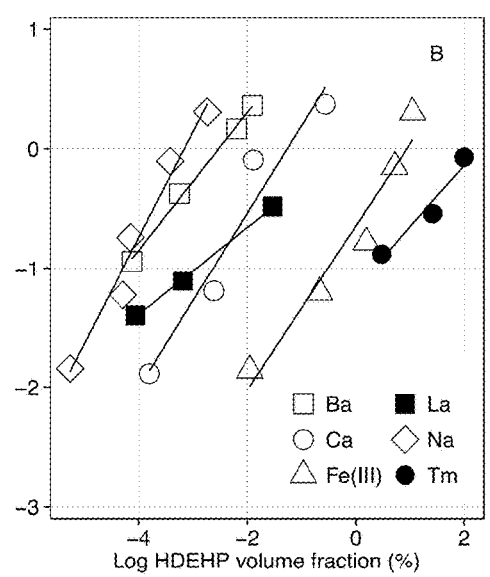

FIG. 8 summarizes the Doehlert design matrix experimental results. Experiment-wise results, with replicates, are presented in FIG. 9. Data for Sc, La, and Gd are not included because these analytes were either not recovered (Sc, which is "irreversibly bound" in the organic phase) or contaminated by a high background (La and Gd; background≥250 ppt in all experiments, see discussion in SI and FIGS. 10A-10B). Subsequent discussion excludes these elements. Across all analytes, median recovery, $\hat{Q}(0.50)=106\%$, was biased high (two-sided Wilcoxon Signed Rank test; $H_0$: $Q(0.5)=100\%$, $P<10^{-6}$). The absolute range of recoveries observed was 83-158% while the 95% credible interval for recoveries was between 92% and 121%. Experiments were generally reproducible (FIG. 9), with element-specific, replicate standard deviations ranging from 0.05% (Nd, experiment 4) to 21% (In, experiment 1). Finally, indium recovery was indistinguishable from any analyte (Wilcoxon, Rank-Sum test; P>0.05), in contrast to recovery from the simple NaCl solutions (FIG. 7). Since these data are not sufficient to determine the mechanism by which this disparity was overcome, the application of indium as a tracer of REE, recovery by the LLE method in unknown samples requires further study. The contrast in HREE recovery between the NaCl-only solutions and these brines with additional complexity may be explained by the partitioning of DOC (pentanoic acid) into the heptane phase. The addition of pentanoic acid would increase the overall polarity of the organic phase, which would weaken the interaction between the polar tails of the HDEHP extractant and the bulk organic diluent (heptane), possibly enriching the interface between organic and aqueous phases with the REE-HDEHP complexes and improving elution.

Figure 11:
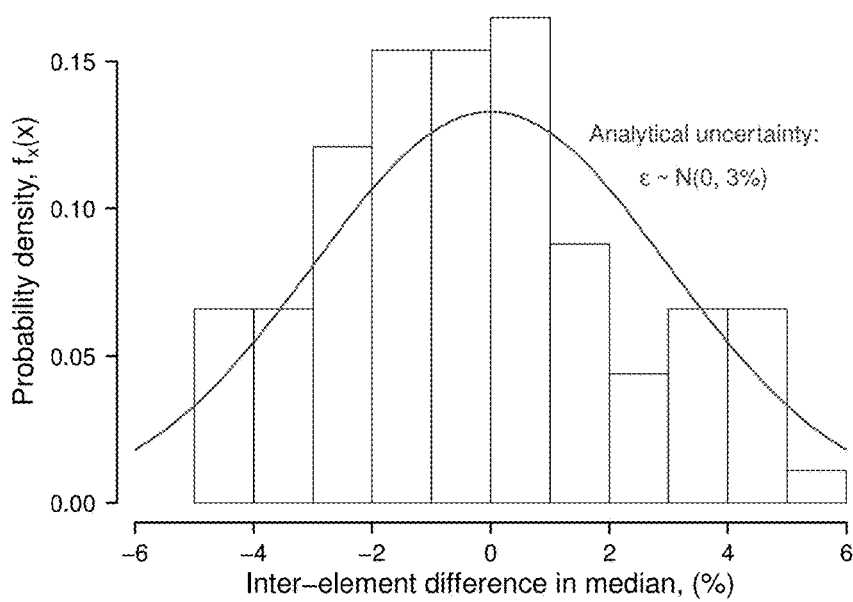
FIG. 11 illustrates the comparison of pair-wise, inter-element differences in median (estimated from the paired-sample Wilcox signed rank test) to the expected (normal) distribution of 3% analytical uncertainty.

The data in FIG. 8 (and FIG. 9) indicate no clear fractionation (or mass bias) of the method across the suite of REE. This result is confirmed by the Kruskal-Wallis test, which found no significant differences between any two element recoveries ($H_0$: No differences in element medians, P>0.1). Pairwise element testing (corrected for multiple comparisons) found statistically significant differences (P<0.05) between 16 element pairs. However, the differences were essentially indistinguishable from 3% analytical error (FIG. 11).

This result differs from those observed in experiments with simple NaCl solutions, where Yb and Lu recoveries were significantly lower at 5 m NaCl. These results showed no observable effects from the studied brine components (i.e. salinity, Fe, and DOC). This finding was confirmed by step-wise regression analysis, which revealed no combination of linear- or interaction-terms among the study variables that substantially influenced recovery. If the solution composition did have any impact on recovery it indistinguishable from replicate variability. These results give confidence to the application of the LLE methodology for natural samples with chemical characteristics within the bounds of the variables studied here, though accurate characterization of the REE concentration of unknown samples may require multiple replicates.

Based on the results presented here, the modified LEE technique represents an attractive option for determination of REE in natural, hypersaline, and chemically complex brines. However, it is critical to have accurate characterization of the samples of interest, as well as the oxide formation rates for the ICP-MS. For samples with low Ba (i.e. a molar [Ba]:[Eu]<$10^5$ in raw samples), the addition of $H_2SO_4$ for barite precipitation is likely unnecessary if the available analytical instrumentation can maintain a $BaO^+$ formation rate on the order of 0.1%. Samples with salinities and/or compositions outside of the range validated here may need to be tested with synthetic brines by the user.

Supplemental Information

SI1. Barium Removal

Figure 2A:
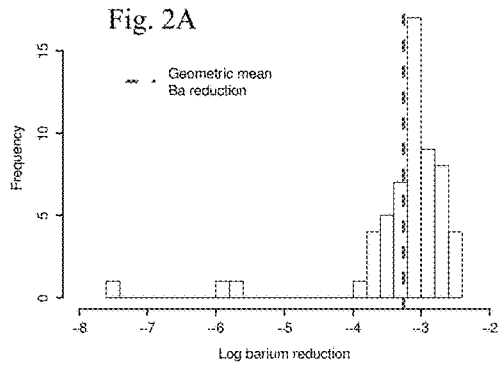
FIGS. 2A-2D present the efficiency of Ba removal by LLE method (FIGS. 2A, 2C) using an Inductively-Coupled Plasma Mass Spectrometer (ICP-MS) equipped with an octopole collision cell for analysis (FIGS. 2B, 2D). Results are for samples without (FIGS. 2A, 2C) and with (FIGS. 2B, 2D) $H_2SO_4$ addition to precipitate barite.
Figure 2B:
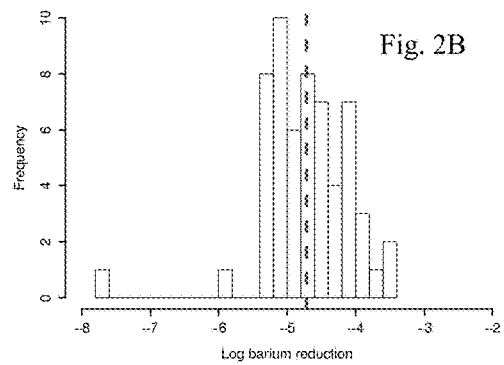
Figure 2C:
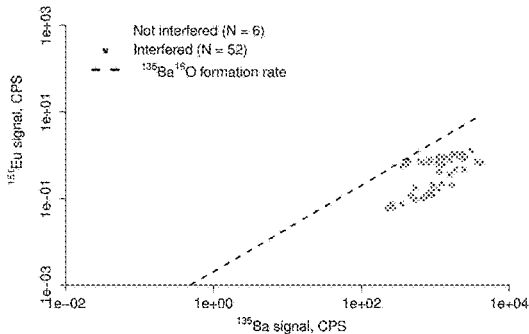
Figure 2D:
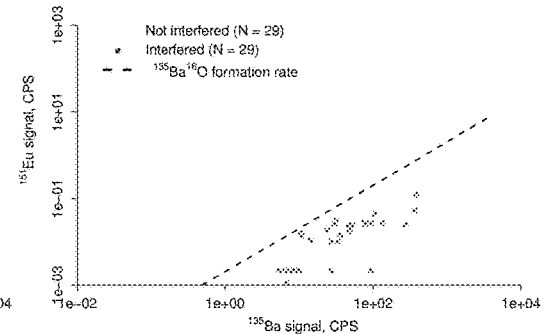
Figure 3:
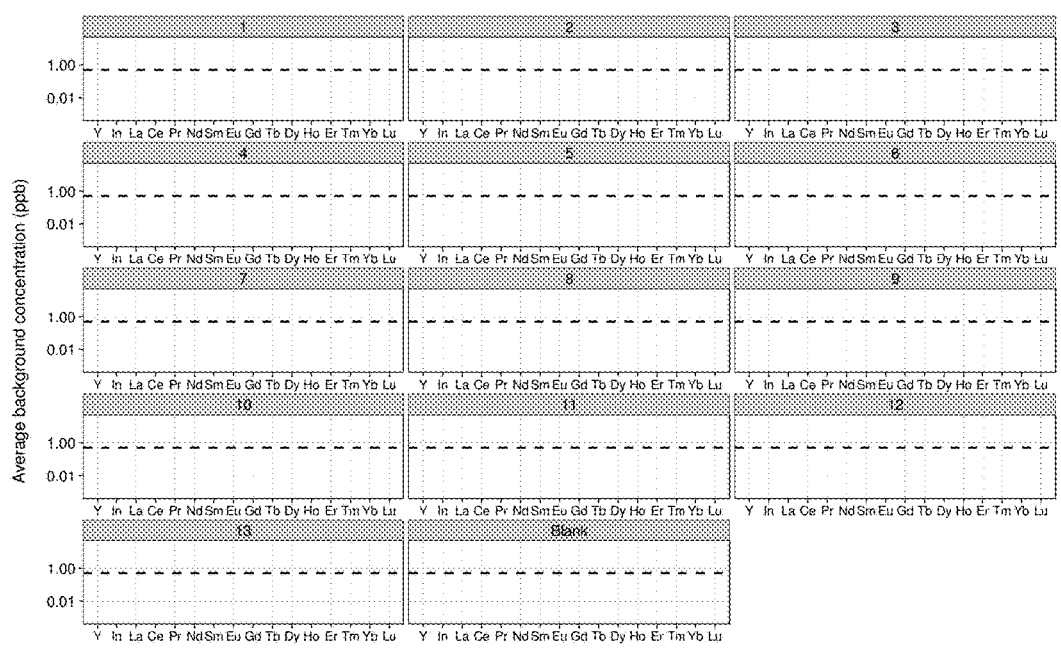
FIG. 3 presents average (from n≥2 replicates, except for Blank and experiments 6, 13) background concentrations of target analytes in samples without $BaSO_4$ precipitation. Dashed line at 500 ppt indicates the input concentration for all spiked samples.

A primary objective in analyzing REE in natural water samples is the separation of Ba, which may lead to isobaric interferences with Eu. FIG. 2A illustrates the effective rejection of Ba by the LLE method presented here, however FIG. 2C shows that even with ~0.2% $^{135}Ba^{16}O^+:1^{35}Ba^+$, the $^{151}Eu^+$ is indistinguishable from $^{135}Ba^{16}O^+$ in the vast majority of samples prior to barite precipitation. Following precipitation (FIGS. 2B, 2D), these issues are resolved.

SI2. Background REE Concentration

Other experimental work in the shared lab space involves high concentrations (~mM) of Gd. The uniformly high Gd background in all experiments is ascribed to cross contamination in this shared space. In the "Blank" experiment (i.e. pH adjusted ASTM Type I water), all analytes were below detection (IDL ~5-20 ppt for 1% false negative rate) except for Ba, La, and Gd. This indicates that the high La background could either be a result of laboratory cross-contamination (as with Gd) or an impurity in the organic phases used. The latter supposition was investigated by direct contact of the mixed organic phases used (i.e. 3 mL 0.25 M HDEHP in heptane+1 mL octanol) with 4 mL of 6 N HCl, followed by analysis of the acid phase. These results were below detection, indicating no significant REE contamination of the organic phases. While all chemicals were purchased at high purity (see SI4), we can assume that the observed background concentrations in other experiments are due to trace contamination of these reagents. Paradoxically, the level of these contaminations cannot be determined without apply a separation/preconcentration technique such as the LLE method; this makes source apportionment of the observed background concentration challenging.

SI3. Internal-External Standardization for Analytical Corrections

For each sample a 2 mL aliquot was spiked with 2 mL of a mixed element standard (5% $HNO_3$ background) while a separate 2 mL aliquot was diluted with 2 mL of blank 5% $HNO_3$. These solutions were analyzed sequentially to examine sample-specific matrix effects and were followed by a 5% $HNO_3$ flush. At the beginning of each analysis run and after every third sample, two separate standard solutions and an analytical blank were analyzed to monitor instrument drift and isobaric, polyatomic interferences (e.g. $^{135}Ba^{16}O^+$ on $^{151}Eu^+$ and light REE-oxides on heavy REE). Eight, serially-diluted, multi-element standard solutions ranging in concentration from 50 ppt to 100 ppb were analyzed at the beginning and end of each run to confirm the linearity assumed by the internal/external calibration.

SI4. Chemical Purity and Suppliers

For the LLE, n-heptane (Chromasolv®; Lot #SHBC0837V), 1-octanol (Chromasolv®; Lot #SHBC6245V), and HDEHP (99.7% purity; Lot #MKBK0176V) were acquired from Sigma Aldrich. Nitric acid ($HNO_3$; BDH ARISTAR® Plus, VWR; assay 69 wt. %; Lot #1113050) was used for sample pH adjustment and as the solvent for all analyses. Hydrochloric acid (HCl; ARISTAR® Plus, VWR; 35 wt. %; Lot #4113083) was used for matrix rinsing and REE back-extraction in the LLE. Chloride salts of Na (Sigma Aldrich; ≥99% purity), Ba (Alfa Aesar; ≥9.998% purity), and Fe (Sigma Aldrich; ≥99.9% purity, trace metal basis) and valeric acid (Alfa Aesar; 99% purity) were used for preparation of synthetic brines. Single element standard solutions (1000 µg/L) of the REE and all elements necessary for internal and external standardization were obtained from Inorganic Ventures. Polypropylene (PP) centrifuge tubes were used in the LLE and glass volumetric flasks were used to prepare organic phases.

SI5. ICP-MS Operating Parameters

TABLE S1

Typical operating conditions for ICP-MS analysis. Analysis performed on Agilent 7700x using oxygen-free argon as the carrier and dilution gas and ultra-high-purity helium in the reaction cell. Conditions determined using 1000:1 diluted Agilent tuning solution. For elements where multiple mass-to-charge ratios were monitored, $^{148}Sm$, $^{151}EU$, and $^{157}Gd$ were used in data analysis.

| | Parameter | Value |
|---|---|---|
| Plasma | RF Power | 1600 W |
| | Nebulizer pump rate | 0.10 rps |
| | Carrier argon flow rate | 0.61 L/min |
| | Dilution argon flow rate | 0.36 L/min |
| Lenses | Extract 1 | 0.0 V |
| | Extract 2 | −200.0 V |
| | Omega bias | −110 V |
| | Omega lens | 9.6 V |
| | Cell entrance | −110 V |
| | Cell exit | −150 V |
| | Deflect | −74.8 V |
| | Plate bias | −150 V |
| Octopole reaction cell | Octopole bias | −100.0 V |
| | Octopole RF | 200 V |
| | He flow rate | 10.0 mL/min |
| | Energy discrimination | 7.0 V |
| Data acquisition | Replicates | 5 |
| | Integration time | 0.3 s |
| Masses monitored | $^{45}Sc$, $^{89}Y$, $^{115}In$, $^{135}Ba$, $^{137}Ba$, $^{139}La$, $^{140}Ce$, $^{141}Pr$, $^{145}Nd$, $^{147}Sm$, $^{148}Sm$, $^{151}Eu$, $^{153}Eu$, $^{157}GD$, $^{158}GD$, $^{159}TD$, $^{163}Dy$, $^{165}Ho$, $^{167}Er$, $^{169}Tm$, $^{173}Yb$, $^{175}Lu$ | |
| Oxides and doubly charged | $^{156}CeO^+/^{140}Ce^+ < 2.1\%$ $^{70}Ce^{2+}/^{140}Ce^+ < 1.6\%$ | |

SI6. Preparation of Synthetic Brines

Chloride salts of Na, Ba, and Fe were dissolved to produce the desired compositions. Dissolved organic carbon was modeled with pentanoic (or valeric) acid, a common component of deep, saline brines, with representative metal-complexing functionality. Additionally, organic acids have also been shown to be a significant component of DOC in produced waters from the Marcellus Shale.

The sensitivity of REE recovery to these parameters was investigated through a uniform shell (or Doehlert), three-factor design matrix, a technique commonly employed for analytical method optimization. The parameters of interest—concentrations of NaCl, Fe, and DOC—were scaled linearly. Experimental conditions for variability in salinity, Fe concentration, and DOC concentration are given in Table S2. For all experiments the concentration of each REE (along with indium) was set at 500 ppt (parts per trillion), a value that falls between the 45th percentile (for Tm) and the 1st percentile (for La) of natural REE distributions in groundwater. Total dissolved Ba was held constant at 2,000 ppm, roughly the average concentration observed by Barbot, et al. for Marcellus Shale produced waters.

TABLE S2

Doehlert experimental design matrix for LLE validation in chemically complex brines. Doehlert coding for each experiment are given in parentheses next to the parameter value. All variables were varied arithmetically.

| Exp | [NaCl] (m) | [Fe] (ppm) | [DOC] (ppm) |
|---|---|---|---|
| 1 | 2 (0) | 40 (0) | 200 (0) |
| 2 | 3.5 (1) | 40 (0) | 200 (0) |
| 3 | 2.75 (0.5) | 74.6 (0.866) | 200 (0) |
| 4 | 2.75 (0.5) | 51.6 (0.289) | 363 (0.817) |
| 5 | 0.5 (−1) | 40 (0) | 200 (0) |
| 6 | 1.25 (−0.5) | 5.4 (−0.866) | 200 (0) |
| 7 | 1.25 (−0.5) | 28.4 (−0.289) | 37 (−0.817) |
| 8 | 2.75 (0.5) | 5.4 (−0.866) | 200 (0) |
| 9 | 2.75 (0.5) | 28.4 (−0.289) | 37 (−0.817) |
| 10 | 1.25 (−0.5) | 74.6 (0.866) | 200 (0) |
| 11 | 2 (0) | 63.1 (0.577) | 37 (−0.817) |
| 12 | 1.25 (−0.5) | 51.6 (0.289) | 363 (0.817) |
| 13 | 2 (0) | 16.9 (−0.577) | 363 (0.817) |

SI7. Recovery of REE, Using Previously Published LLE Conditions

Figure 4:
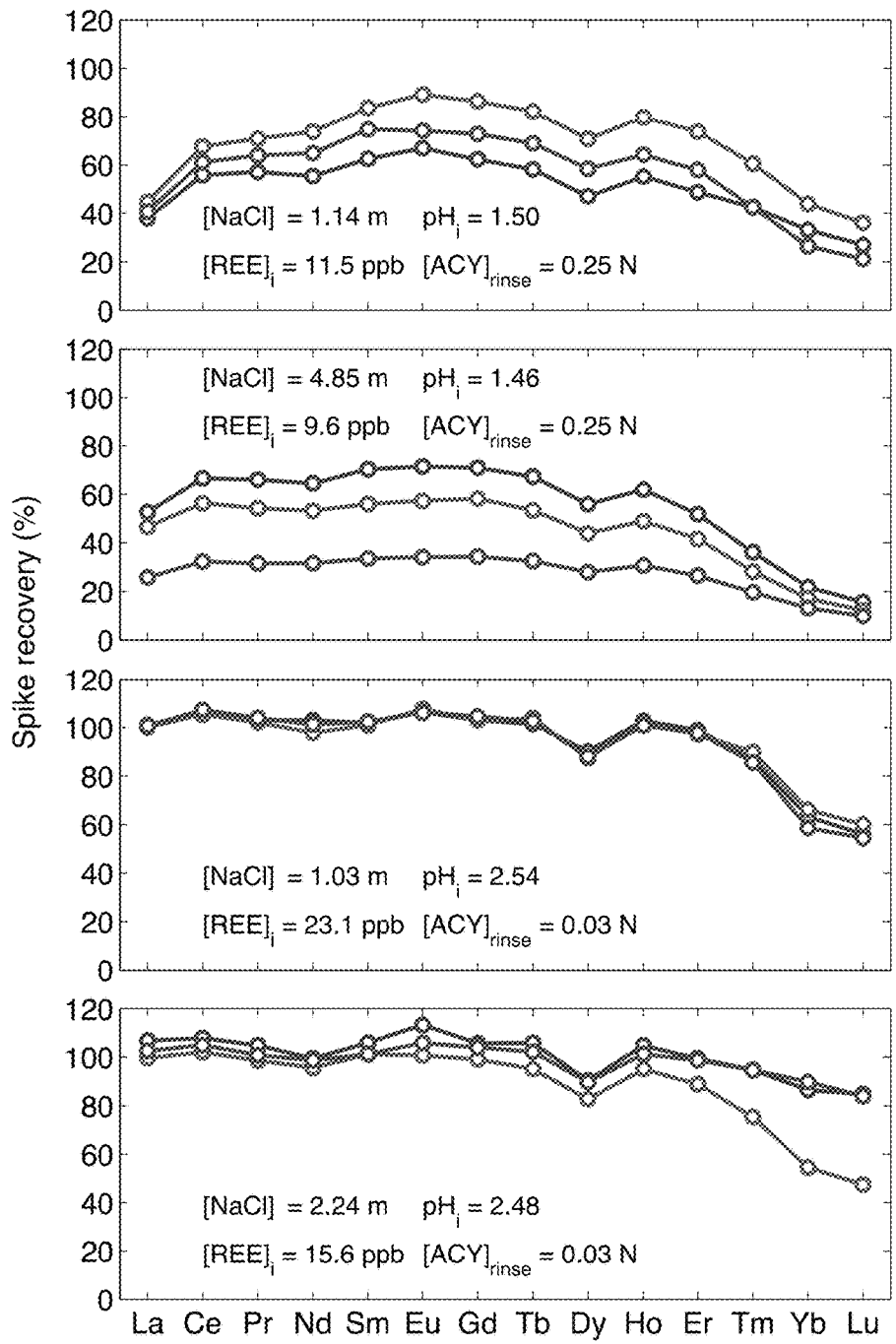
FIGS. 4A-4D displays the REE recovery from 10 g samples of synthetic brine solutions using LLE conditions recommended by a prior art method (FIGS. 4A, 4B) and "optimal" conditions predicted by multiple linear regression (FIGS. 4C, 4D).
Figure 5:
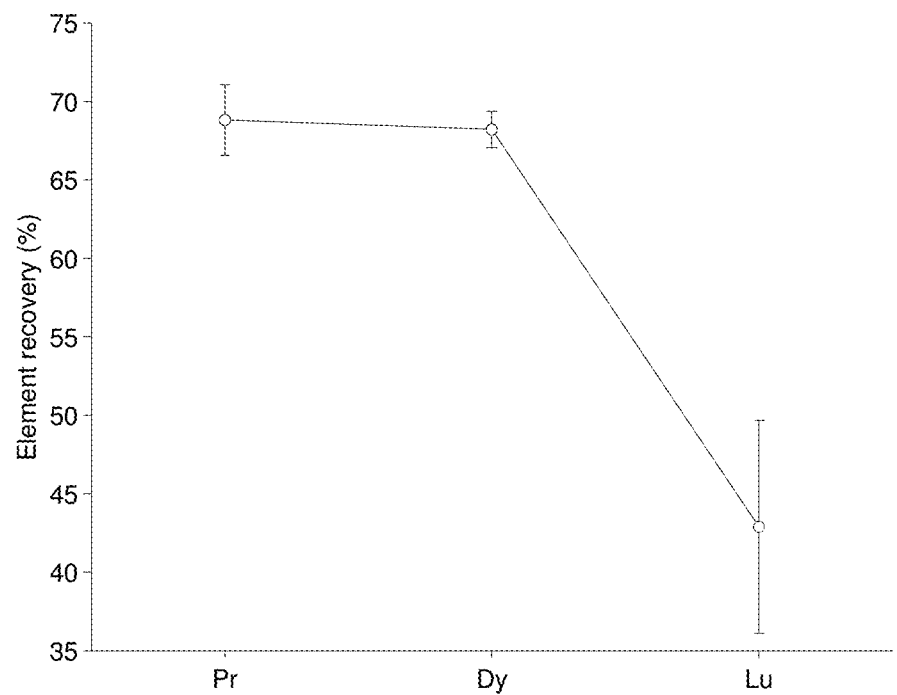
FIG. 5 shows the recovery of select REE from 1 m NaCl solutions (100 ppb REE initial) by LLE method with recommended operating conditions, using mixed mono- and diester phosphoric acid ligand in heptane (0.25 M total, approximate mono-to-diester mass ratio of 35:65). Results are from triplicate experiments and represent the mean recovery one standard deviation.

The recommended operating conditions lead to MREE-preferred fractionation of the REE in synthetic brine samples (FIGS. 4A, 4B). In general, the MREE were recovered 10-20% more efficiently than either the LREE, or HREE. Experimental replicates also showed considerable variability, indicating that the kinetics and thermodynamics of the separation may be highly sensitive at the recommended operating conditions. A Wilcoxon rank sum test between experiments at two salinities (1.14 and 4.85 m NaCl; FIGS. 4A and 4B respectively) determined recovery was diminished in the increased salinity experiment ($H_0$: No difference in median recovery; $P<10^{-4}$). However, the magnitude of this decrease—quantified by the Hodges-Lehmann (H-L) estimator in $R^3$—was uncertain, with REE recovered between 8.14% and 25.1% less efficiently (95% confidence interval of the H-L estimator) in the higher salinity experiment.

While the disclosure has been described in detail and with reference to specific embodiments thereof, it will be apparent to one skilled in the art that various changes and modification can be made therein without departing from the spirit and scope of the embodiments. Thus, it is intended that the present disclosure cover the modifications and variations of this disclosure provided they come within the scope of the appended claims and their equivalents.

What is claimed is:

1. A method of recovering rare earth elements from a brine solution containing interfering compounds using liquid-liquid extraction techniques, the method comprising:
   performing a forward extraction to partition the rare earth elements from the brine solution to an organic phase using bis(2-ethylhexyl) phosphate as the extractant in a heptane diluent,
      wherein an operating condition during the forward extraction is adjusted to achieve a log $K_d>1.6$, wherein $K_d$ is the partition coefficient between the organic phase and the brine solution,
      wherein the rare earth elements are complexed with the extractant; and
   performing a backward extraction on the organic phase to partition the complexed rare earth elements to an aqueous phase.

2. The method of claim 1, wherein the operating condition comprises at least one of initial acidity and extractant concentration.

3. The method of claim 2 further comprising optimizing the operating conditions based on an equilibrium-partitioning model.

4. The method of claim 3, wherein the model comprises:
   a partition coefficient between the organic phase and the brine solution as a function of acidity and extractant volume fraction.

5. The method of claim 1, further comprising:
   dosing the aqueous phase with concentrated sulfuric acid to precipitate barium as barite.

6. The method of claim 5, further comprising:
   analyzing the rare earth elements in the aqueous phase.

7. The method of claim 1, wherein the brine solution has an ionic strength greater than 0.7 M NaCl.

8. The method of claim 7, wherein the brine solution has an ionic strength up to 5 M NaCl.

9. The method of claim 1, wherein the backward extraction step further comprises:
   adding 1-octanol to the organic phase; and
   stripping the rare earth elements from the organic phase with acid.

10. The method of claim 9, wherein the acid comprises 6.0 N HCl.

11. The method of claim 1, wherein adjusting the operating condition comprises decreasing the initial acidity to $<10^{-2}$ N.

12. The method of claim 1, further comprising:
   adjusting an operating condition during the backward extraction to achieve a log $K_d<-1.2$, wherein $K_d$ is the partition coefficient between the organic phase and the aqueous phase.

13. The method of claim 1, further comprising:
   rinsing the aqueous phase with heptane to remove dissolved organics from the aqueous phase.

14. The method of claim 1, further comprising:
   rinsing the organic phase with an acid to remove matrix and interfering species present in the brine solution.

15. The method of claim 14, further comprising:
   adjusting a rinse acidity to achieve a log $K_d>1.4$ in the rinsing step, wherein $K_d$ is the partition coefficient between the organic phase and the acid.

16. The method of claim 15, wherein adjusting the rinse acidity comprises decreasing an acidity to $<10^{-1.5}$ N.

17. The method of claim 1, further comprising:
   excluding Na and Ba during forward extraction.

* * * * *